US00PP21648P2

(12) United States Plant Patent
Hurkman

(10) Patent No.: US PP21,648 P2
(45) Date of Patent: Jan. 18, 2011

(54) ***PETUNIA* PLANT NAMED 'BALSUNBUR'**

(50) Latin Name: *Petunia×hybrida*
Varietal Denomination: Balsunbur

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/583,876

(22) Filed: Aug. 27, 2009

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP14,346 P2 * 12/2003 Hanes ..... Plt./356
PP15,310 P2 * 11/2004 Westhoff ..... Plt./356

OTHER PUBLICATIONS

UPOV ROM GTITM Computer Database, GTI Jouve Retrieval Software 2010/03 Ciation for 'Balsunbur'.*

* cited by examiner

*Primary Examiner*—Wendy C. Haas
(74) *Attorney, Agent, or Firm*—Audrey Charles

(57) ABSTRACT

A new and distinct cultivar of *Petunia* plant named 'Balsunbur', characterized by its burgundy-colored flowers, medium green-colored foliage, and vigorous, mounded-trailing growth habit, is disclosed.

1 Drawing Sheet

Latin name of genus and species of plant claimed: *Petunia×hybrida.*

Variety denomination: 'Balsunbur'.

BACKGROUND OF THE INVENTION

The present invention relates to a new and distinct cultivar of *Petunia* plant botanically known as *Petunia×hybrida* and hereinafter referred to by the cultivar name 'Balsunbur'.

The new cultivar originated in a controlled breeding program in Arroyo Grande, Calif. during October 2004. The objective of the breeding program was the development of *Petunia* cultivars with single type flowers, unique flower coloration, and a vigorous, mounded-trailing growth habit.

The new *Petunia* cultivar is the result of cross-pollination. The female (seed) parent of the new cultivar is the proprietary *Petunia×hybrida* breeding selection designated 2840-1, not patented, characterized by its dark burgundy-colored flowers, medium green-colored foliage, and moderately vigorous, semi-upright growth habit. The male (pollen) parent of the new cultivar is Jamboree Burgundy 'Jam Burg', U.S. Plant Pat. No. 14,346, characterized by its dark burgundy-colored flowers, medium green-colored foliage, and moderately vigorous, compact growth habit. The new cultivar was discovered and selected as a single flowering plant within the progeny of the above stated cross-pollination during July 2005 in a controlled environment at Arroyo Grande, Calif.

Asexual reproduction of the new cultivar by terminal stem cuttings since July 2005 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsunbur' as a new and distinct cultivar of *Petunia* plant:

1. Burgundy-colored flowers;
2. Medium green-colored foliage; and
3. Vigorous, mounded-trailing growth habit.

Plants of the new cultivar differ from plants of the female parent primarily in flower size, leaf size, and growth habit. The new cultivar has a larger flower, smaller leaf and a more trailing growth habit than plants of the female parent.

Of the many commercially available *Petunia* cultivars, the most similar in comparison to the new cultivar is the male parent Jamboree Burgundy 'Jam Burg', U.S. Plant Pat. No. 14,346. However, in side by side comparisons, plants of the new cultivar differ from plants of 'Jam Burg' in at least the following characteristics:

1. Plants of the new cultivar have a lower surface petal color different from plants of 'Jam Burg';
2. Plants of the new cultivar have longer peduncles than plants of 'Jam Burg'; and
3. Plants of the new cultivar have a petal apex different from plants of 'Jam Burg'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsunbur'. The plants were grown in 4.5 inch pots for 11 weeks in a greenhouse at West Chicago, Ill.

DETAILED BOTANICAL DESCRIPTION

Figure 1:
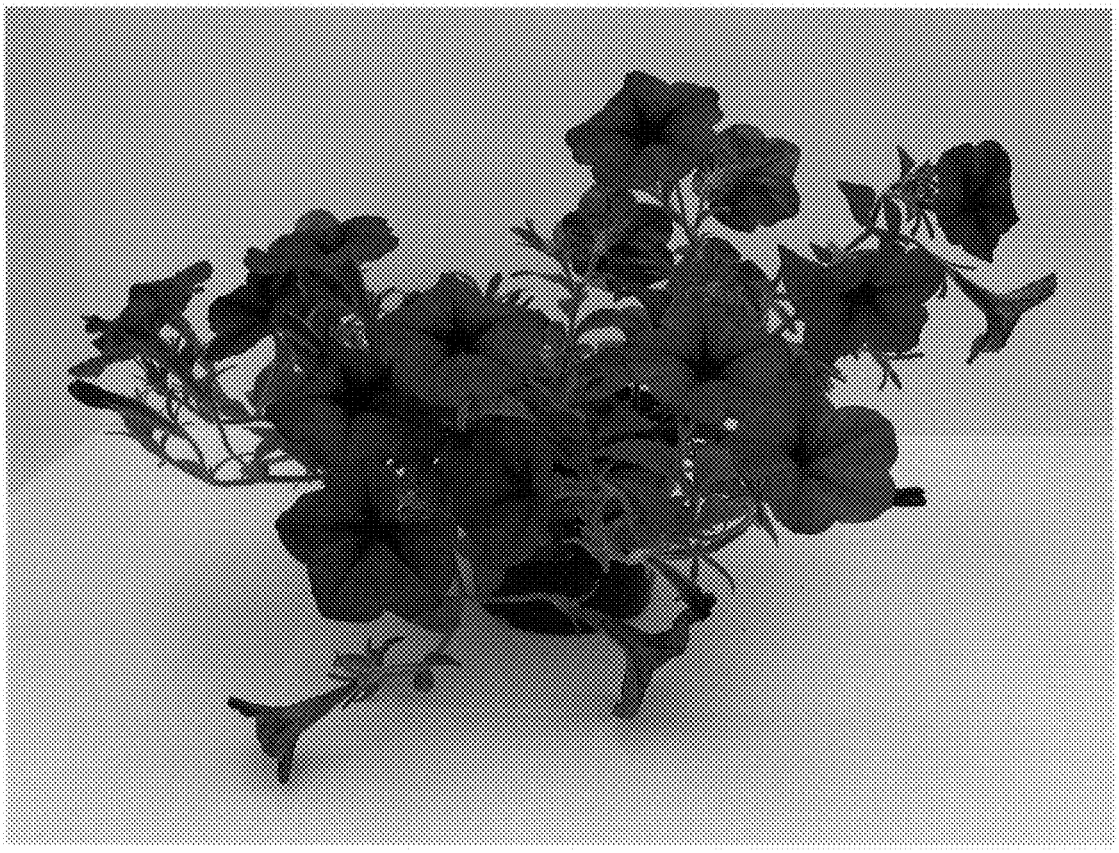
FIG. 1 illustrates a side view of the overall growth and flowering habit of 'Balsunbur'.
Figure 2:
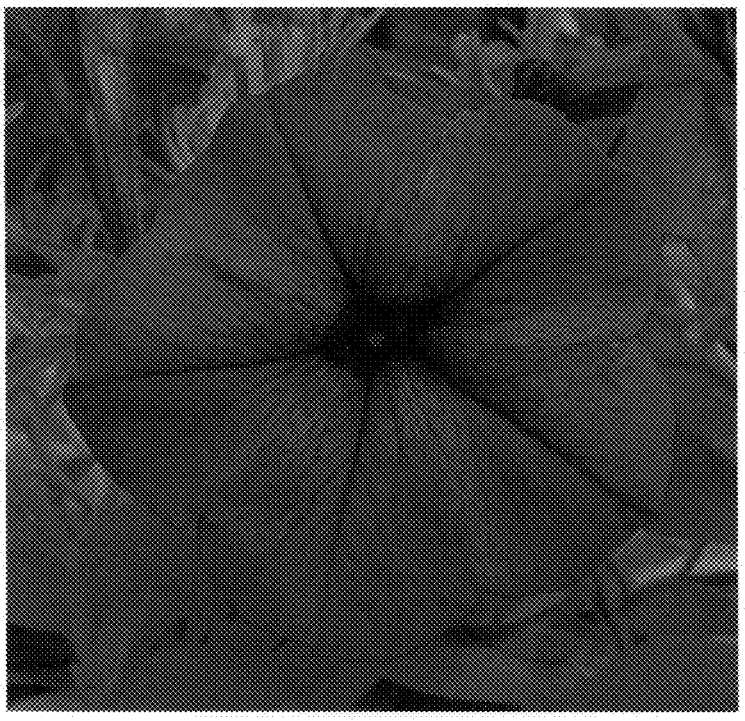
FIG. 2 illustrates a close-up view of an individual flower of 'Balsunbur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in July 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification.—*Petunia×hybrida* cultivar Balsunbur.

Parentage:

*Female parent.*—Proprietary *Petunia×hybrida* breeding selection designated 2840-1, not patented.

*Male parent.*—Jamboree Burgundy 'Jam Burg', U.S. Plant Pat. No. 14,346.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Vigorous, mounded-trailing.

*Size.*—Height from soil level to top of plant plane: Approximately 16.3 cm. Width: Approximately 48.6 cm.

*Branching habit.*—Freely branching, pinching improves basal branching. Quantity of main branches per plant: Approximately 5.

*Branch.*—Strength: Moderate. Length: Approximately 29.4 cm. Diameter: Approximately 3.0 mm. Length of central internode: Approximately 2.8 cm. Texture: Densely glandular pubescent with a mixture of long and short length hairs. Gland color: Colorless. Color of young and mature stems: 144A.

Foliage description:

*General description.*—Quantity of leaves per main branch: Approximately 18. Fragrance: Slight. Form: Simple. Arrangement on flowering stem: Opposite.

*Leaves.*—Aspect: Perpendicular to acute angle to stem. Shape: Ovate. Margin: Entire. Apex: Acute. Base: Attenuate. Venation pattern: Pinnate. Length of mature leaf: Approximately 5.8 cm. Width of mature leaf: Approximately 3.0 cm. Texture of upper and lower surfaces: Moderately glandular pubescent. Gland color: Colorless. Color of upper surface of young foliage: 137C with venation of 144B. Color of lower surface of young and mature foliage: 138B with venation of 144B. Color of upper surface of mature foliage: 137A with venation of 144B.

*Petiole.*—Length: Approximately 5.0 mm. Width: Approximately 2.0 mm. Texture: Densely glandular pubescent with a mixture of long and short length hairs. Gland color: Colorless. Color: 144B.

Flowering description:

*Flowering habit.*—'Balsunbur' is freely flowering under outdoor growing conditions with substantially continuous blooming from spring through autumn and year-round in greenhouse environment.

*Lastingness of individual flower on the plant.*—Approximately 10 to 12 days.

Flower description:

*General description.*—Type: Simple, salverform. Quantity per plant: Approximately 19. Fragrance: Slight.

*Bud.*—Rate of opening: Generally takes 2 to 3 days for bud to progress from first color to fully open flower. Quantity per plant: Approximately 8.

*Bud just before opening.*—Shape: Oblong. Length: Approximately 4.9 cm. Diameter at apex: Approximately 7.0 mm. Diameter at base: Approximately 3.0 mm. Texture: Densely glandular pubescent. Gland color: Colorless. Color of petals: 79B with venation of N77A. Color of tube: N77B with venation of N77A.

*Corolla.*—Diameter: Approximately 6.5 cm.

*Petals.*—Quantity: 5, fused to form a tube. Shape: Obovate. Appearance: Velvety. Margin: Entire, wavy. Apex: Rounded. Length from tube: Approximately 3.1 cm. Length of free portion: Approximately 1.1 cm. Width: Approximately 3.4 cm. Texture of upper surface: Glabrous. Texture of lower surface: Sparsely glandular pubescent. Color of upper surface when first and fully open: Darker than and more purple than N74A; venation of N92A. Color of lower surface when first and fully open: 77B with areas of 79C nearest venation; venation of N77A.

*Corolla tube.*—Length: Approximately 3.8 cm. Diameter at distal end: Approximately 1.0 cm. Diameter at proximal end: Approximately 3.0 mm. Texture of inner surface: Glabrous. Texture of outer surface: Densely glandular pubescent. Gland color: Colorless. Color of inner surface: 79A with venation of N92A. Color of outer surface: 79C with venation of N77A.

*Sepals.*—Quantity per flower: 5, fused at base. Shape: Linear. Apex: Acute. Length: Approximately 2.2 cm. Width: Approximately 2.0 mm. Texture of upper and lower surfaces: Densely glandular pubescent. Color of upper surface: 137A transitioning to 144A at base. Color of lower surface: 137C transitioning to 144A at base.

*Peduncle.*—Strength: Strong. Aspect: Acute angle to stem. Length: Approximately 3.5 cm. Diameter: Approximately 2.0 mm. Texture: Densely glandular pubescent with a mixture of long and short length hairs. Gland color: Colorless. Color: 144A often with a faint overlay of 187B nearest flower attachment.

*Reproductive organs.*—Androecium: Stamen quantity: 5, basifixed. Stamen length: Approximately 2.6 cm. Filament length of fixed portion: Approximately 1.1 cm. Filament color: 155D with an overlay of N79D. Anther shape: Bilobed. Anther length: Approximately 1.0 mm. Anther color: N92C. Pollen amount: Abundant. Pollen color: 93D. Gynoecium: Pistil quantity: 1 per flower. Pistil length: Approximately 2.8 cm. Stigma shape: Funnel. Stigma length: Approximately 2.0 mm. Stigma color: N92A. Style length: Approximately 2.3 cm. Style color: 145B with an overlay of N79D toward stigma. Ovary length: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balsunbur', substantially as herein shown and described.

* * * * *